United States Patent [19]

Bremer et al.

[11] Patent Number: 5,261,873
[45] Date of Patent: Nov. 16, 1993

[54] HALO VEST AND LINING

[75] Inventors: Paul Bremer; Ross L. Bremer, both of Jacksonville, Fla.

[73] Assignee: Acromed Inc., Jacksonville, Fla.

[21] Appl. No.: 474,288

[22] Filed: Feb. 5, 1990

[51] Int. Cl.$^5$ .............................................. A61F 5/09
[52] U.S. Cl. ........................................ 602/32; 602/5; 602/36; 128/869
[58] Field of Search ............... 128/68, 76 R, 78, 83, 128/84 R, 89 A, 874, 75, 87 B, 869, 870, 875, 876; 602/5, 17, 18, 19, 20, 32, 36, 37, 38

[56] References Cited

U.S. PATENT DOCUMENTS

| | | | |
|---|---|---|---|
| 3,717,143 | 2/1973 | Johnson | 128/78 |
| 4,043,325 | 8/1977 | Ochs et al. | 128/87 B X |
| 4,515,153 | 5/1985 | Calabrese | 128/75 |
| 4,620,530 | 11/1986 | Lanier et al. | 128/75 |
| 4,628,913 | 12/1986 | Lepman | 128/68 X |
| 4,913,135 | 4/1990 | Mattingley | 128/75 X |

OTHER PUBLICATIONS

Bremer Orthopedics "Halo Vest" flyer; 1987, Bremer Orthopedics, Inc.

Primary Examiner—Robert A. Hafer
Assistant Examiner—Sam Rimell
Attorney, Agent, or Firm—Nixon & Vanderhye

[57] ABSTRACT

A halo vest (for cervical and spine injuries) having a body of structural material such as hard plastic has halo supporting rods and a halo attached to it. A lining of wicking material is provided for the vest body. The vest body has a surface configuration that avoids pressure on bony prominences, has flat surfaces at flat bone areas and curved surfaces at curved bone areas of the user, and exerts less than about seven pounds per square inch pressure on the wearer's skin. No dimension from an interior surface point to the closest peripheral portion is larger than the ability of the lining to readily wick liquid from the interior surface point to the peripheral portion so as to avoid skin wetness. The lining comprises a first layer of water proof and vapor proof material like cross-linked closed cell polyethylene foam having grooves to facilitate transport of liquid toward the periphery of the vest, and a second layer of soft, wicking textile material that is air, water, and vapor permeable. The textile material, such as a bunting material about one-quarter inch thick, is releasably attached (e.g. with hook and loop fasteners) to the vest body interior surface.

20 Claims, 2 Drawing Sheets

HALO VEST AND LINING

BACKGROUND AND SUMMARY OF THE INVENTION

A halo vest is a well known device for patients with cervical or spine injuries, which effectively immobilizes the neck of the wearer to promote healing. Such devices are applied in a medical procedure by an orthopedic surgeon, or like qualified physician, and must be worn by the patient until healing is complete. Sometimes the healing process can take months, in which case hygiene and comfort become significant problems.

Conventional halo vests have fleece (synthetic or lamb's wool) liners. The purpose of the liner is to act as padding, and to allow moisture vapor from the skin to leave the skin and transpire to the outside of the halo vest from underneath the impermeable plastic shell of which the conventional halo vest is constructed. The moisture vapor transfer is necessary since if moisture is held against the skin the skin will breakdown, which can result in ulcer formations on the wearer's skin, or like conditions as a result of constant skin wetness.

The patient cannot take a bath with a fleece liner since it holds water like a sponge. Therefore the patient must be wiped with a damp cloth, which becomes unacceptable after the passage of a certain length of time. The fleece liner cannot be removed by a non-surgical procedure since it also provides padding and the fit of the vest would change drastically with the removal of such a thick material.

According to the present invention it is possible to provide a halo vest, and a liner for a halo vest, which provide for maximum comfort and hygiene. The halo vest according to the invention is constructed such that the maximum straight line dimension from any interior surface point of the vest body to the closest peripheral portion thereof is less than about four inches. This may be accomplished, for example, by forming apertures in the vest shell. Also the vest body has a surface configuration that avoids pressure on bony prominences, has flat surfaces at flat bone areas and curved surfaces at curved bone areas, and exerts less than about seven pounds per square inch pressure on the wearer's skin.

The preferred lining according to the present invention includes a textile wicking material. The lining readily wicks liquid and water vapor from the interior surface of the vest to peripheral portions so as to avoid breakdown of the wearer's skin. Because the vest has no dimension from an interior surface point to the closest peripheral portion larger than the ability of the lining to readily wick liquid, constantly wet skin is avoided. The interior surface of the vest body is flat at the wearer's sternum, and curved at the wearer's ribs, and does not engage the wearer's shoulder blades or spinous processes.

The wicking textile material is provided against the wearer's body and it has sufficient thickness so as to hold liquid therein to minimize skin wetness, but thin enough to be readily removed from the vest while the vest is being worn by a wearer without disturbing the fit of the vest so as to jeopardize the health of the wearer. Typically the textile wicking material is a polypropylene bunting, or the like, for example having a thickness of approximately one-quarter inch. The textile wicking material typically has an MVT of at least about 400 grams per square meter per 24 hours, and an air permeability of at least about 175 ft.$^3$/ft.$^2$/min.

The vest lining according to the invention also preferably comprises another layer in addition to the textile wicking material, which is adjacent the hard plastic shell of the vest body. This other layer is preferably a water proof and vapor proof material that allows lateral movement of air and water vapor with respect to it, such as a closed cell foam (e.g. cross-linked polyethylene foam) having grooves therein to facilitate transport of liquid toward the periphery of the vest.

Utilizing the vest and lining according to the invention, the spine and/or neck injuries of a human patient may be treated by, in a medical procedure, placing the patient in the halo vest with the halo attached to the patient's head; and, in a non-medical procedure, removing at least one layer of the vest lining adjacent the patient's skin on approximately a daily basis, and replacing it with a clean lining while the patient is wearing the halo vest, without removal of the halo vest or jeopardizing the health of the patient. In this way hygiene and comfort are maximized.

It is the primary object of the present invention to provide a halo vest, and method of treating cervical and spine injuries, so that the wearer may have maximum hygiene and comfort. This and other objects of the invention will become clear from an inspection of the detailed description of the invention and from the appended claims.

DETAILED DESCRIPTION OF THE DRAWINGS

Figure 1:
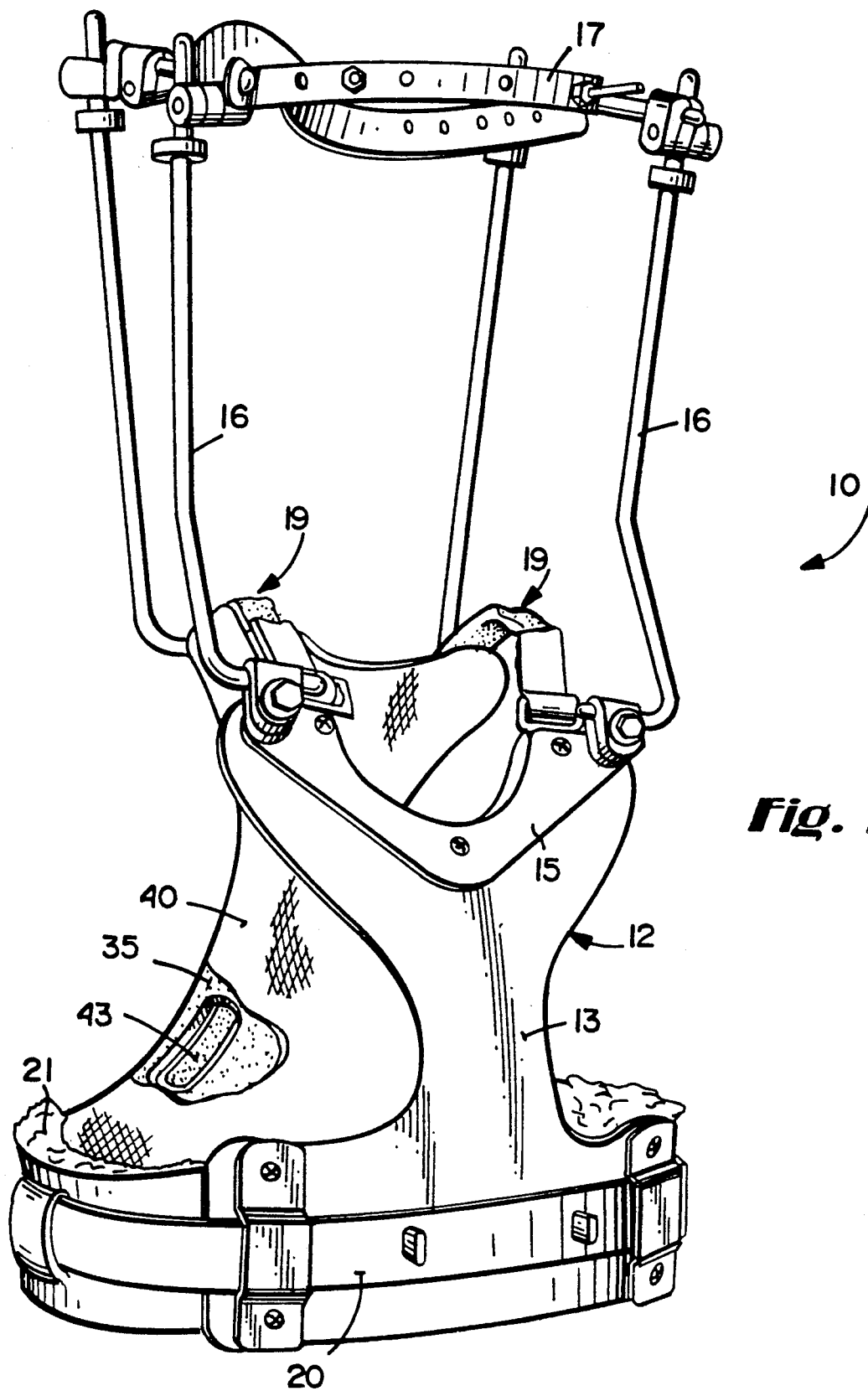
FIG. 1 is a front perspective view of an exemplary halo vest, with exemplary lining, according to the invention.
Figure 2:
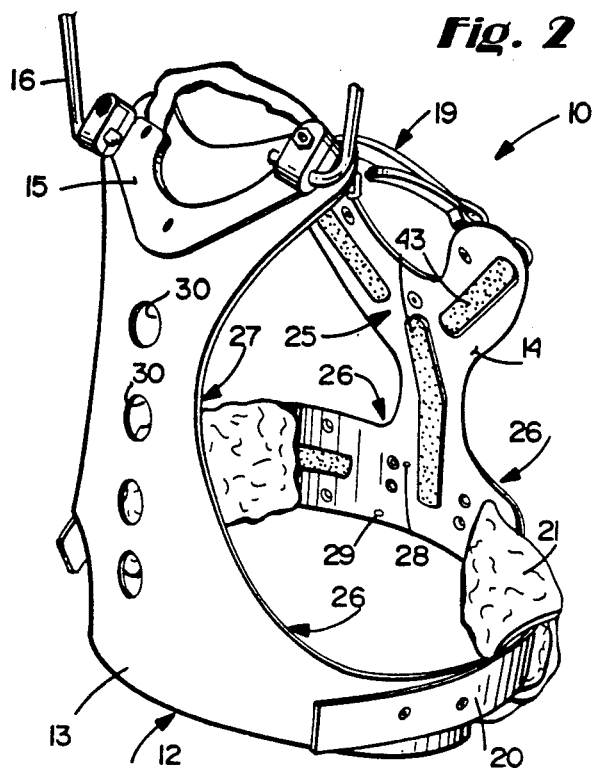
FIG. 2 is a rear perspective view of the vest of FIG. 1 with the lining removed.

An exemplary halo vest according to the invention is shown generally by reference numeral 10 in FIG. 1. The vest includes a vest body 12 of structural material, such as hard plastic, having an exterior surface 13 and an interior surface 14 (FIG. 2). Attached to the halo vest are conventional support plates 15 and support rods 16 (the halo supporting means) for a halo 17 that is placed on a wearer's head in a surgical procedure. The vest body 12 preferably includes front and rear components, as can be seen by an inspection of FIGS. 1 and 2 with adjustable length straps 19 connecting the vest body parts at the top, an adjustable length belt 20 and padding 21 materials connecting the vest components adjacent their bottoms.

The vest body 12 according to the invention has a surface configuration that avoids pressure on bony prominences, has flat surfaces at flat bone areas and curved surfaces at curved bone areas of the patient. It exerts less than about seven pounds per square inch pressure on the wearer's skin. For example the interior surface of the vest body 12 at the wearer's sternum area 25 is substantially flat, while at the wearer's ribs portions 26 it is curved. While the vest completely covers the sternum, and partially covers the ribs, it does not engage the wearer's shoulder blades (merely the adjustable straps 19 being provided), or the spinous processes. At its rear where it might engage the spinous processes it bulges (curves) outwardly, as indicated by reference numeral 27 in FIG. 2, or is absent entirely making a "window" or opening to avoid pressure on spinous processes.

The vest body 12 is also constructed so that it has no dimension from an interior surface point thereof to the closest peripheral portion larger than the ability of the lining with which the vest is used to readily wick liquid from the interior surface point to the peripheral portion. In this way constant wetness of the wearer's skin is avoided. For example, the maximum straight line distance from any interior surface point (e.g. point 28 in FIG. 2) to the nearest peripheral portion (e.g. point 29 in FIG. 2) is less than about four inches, preferably on average less than about three inches. At the back of the vest, e.g. the bulging area 27, means can be provided defining circular or other configuration apertures 30 to ensure the ready wicking ability of the lining. The advantages achieved by the vest are accomplished not just with the outline shape and opening, but also by cross-sectional configuration (curves) that place differential loads against body according to the parts of the body that can bear the most pressure.

According to the present invention an improved lining is also provided. While the lining which will be hereafter described may be utilized even with conventional halo vests, it has its maximum utility when utilized with the improved halo vest 10 illustrated in FIGS. 1 and 2.

Figure 5:
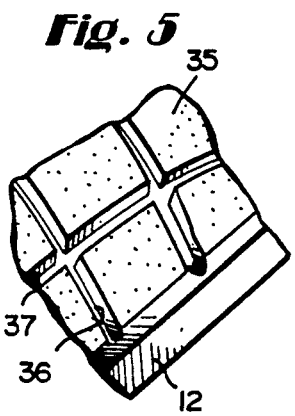
FIG. 5 is a detailed top perspective view of the interior surface of the foam lining portion of the vest of FIG. 4.
Figure 3:
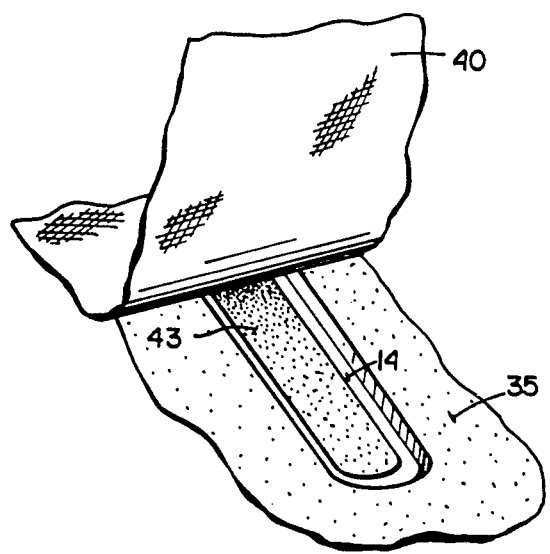
FIG. 3 is an exploded view illustrating an exemplary manner of interconnection between the vest lining material and vest according to the invention.
Figure 4:
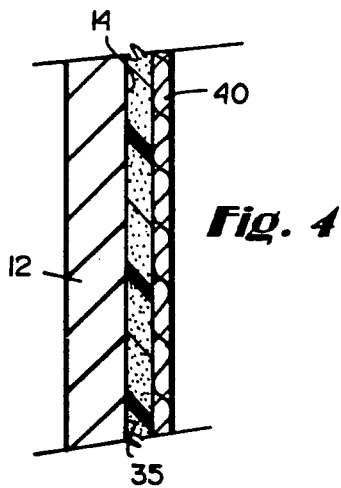
FIG. 4 is a cross-sectional view of the vest with lining materials of the embodiment of FIG. 3.

The lining according to the invention preferably is a multi-layer lining, a first layer which is against the hard plastic shell of the vest body, and a second layer which is against the skin of the patient. FIGS. 3 and 4 most clearly illustrate the combination of the layer components according to the invention. Adjacent the inner surface 14 of the vest body 12 is a first layer 35 comprising a water proof and vapor proof material that allows lateral movement of air and water vapor with respect thereto. Preferably this layer 35 comprises a closed cell foam, such as cross-linked polyethylene foam, with grooves formed therein to facilitate transport of liquid toward the periphery of the vest. FIG. 5 illustrates the foam layer 35 with grooves 36, 37 formed therein. As illustrated in FIG. 5 grooves 36, 37 may be arranged transverse to each other, or in any particular section of the vest body 12 they may be directed so as to provide a straight line path to the nearest peripheral portion (e.g. 29) of the vest body 12. Thus a "sunburst" design, or other configurations of the grooves 36, 37, may be provided.

The second layer of the lining according to the invention comprises a soft wicking sheet of material, such as a textile material, 40. The material 40 overlays the grooved face of the foam 35, and is adjacent the wearer's skin. The material 40 is air, water, and vapor permeable. It has sufficient thickness so as to hold enough liquid therein to minimize the possibility of wetness on the wearer's body, but it is thin enough to be readily removable from the vest 10 while the vest 10 is being worn by a wearer, in a non-medical procedure, without disturbing the fit of the vest so as to jeopardize the health of the wearer. Typically, the textile material 40 would have a thickness of approximately one-quarter inch, an MVT of at least about 400 grams per square meter per 24 hours (ASTM E96), an air permeability of at least about 175 ft.$^3$/ft.$^2$/min. (ASTM D737-75), and has thermal insulation properties. One particularly useful fabric for this purpose is a polypropylene or like bunting material sold by the Malden Company of Malden, N.Y. under the trademark "Polarplus", style 7610. Such as fabric is a double faced fabric that is plush on both sides, won't pill, and can be machine washed without shrinking. It has a weight of about 10–12 ounces per square yard (e.g. 10.8 ounces per square yard), a thickness of about 0.20–0.30 inches, e.g. 0.268 inches, with a width stretch of about 40–45% (e.g. 43.8%), and a width recovery of about 90–100% (e.g. 100%). The moisture vapor transfer is about 479 grams per square meter per 24 hours using ASTM E96, while the air permeability is about 215 ft.$^3$/ft.$^2$/min., using ASTM D737-75.

The second layer 40 is attached to the vest body 12 in a releasable manner. This may be accomplished by using conventional hook fasteners (e.g. Velcro®) in strip form, as illustrated by strips 43 in FIGS. 2 and 3. The hooks of the strips 43 engage loops attached to the textile material 40 to releasably hold the textile material 40 in place. Loop strips of fastener material (e.g. Velcro®) may be provided on the inner surface of the material 40 to cooperate with the hook strips 43. For clarity of illustration, FIG. 2 illustrates the hook strips 43 provided on the vest interior surface 14 with the first layer 35 removed.

While it is preferred that the vest lining according to the invention be a multi-layer lining, under some circumstances it may be possible to use the textile material 40 alone.

Utilizing the vest body 12 and a lining 35/40 according to the invention, a procedure for treating cervical and/or spine injuries using a halo vest, which has increased hygiene and comfort, may be provided. In the practice of such a method, first in a medical procedure, e.g. by an orthopedic or neurological surgeon, the patient is placed in the halo vest 10 with the halo 17 attached to the patient's head. The lining layer 40 is adjacent the wearer's body. In a non-medical procedure, the layer 40 of the vest lining adjacent the patient's skin is periodically removed, e.g. on a daily basis. In the past removal of conventional halo vest linings could only be done in a medical procedure, e.g. at a hospital. The layer 40 is removed merely by pulling it out of engagement with the hook fastener strips 43, and it is pulled between the wearer's body and the vest body 12. It can be replaced with a clean lining, and then washed and utilized again. The clean lining is inserted in the same way, merely by moving the relatively thin lining 40 between the first layer 35 and the wearer's body, whereby it is held in place by the hook strips 43. The replacement of the lining for wearer comfort and hygiene is then accomplished without removal of the halo vest or jeopardizing the health of the patient.

It will thus be seen that according to the present invention an improved halo vest, halo vest lining, and method of treating cervical and/or spine injuries is provided. While the invention has been herein shown and described in what is presently conceived to be the most practical and preferred embodiment, it will be apparent to those of ordinary skill in the art that many modifications may be made thereof within the scope of the invention, which scope is to be accorded the broadest interpretation of the appended claims so as to encompass all equivalent structures and procedures.

What is claimed is:

1. A halo vest for a human wearer, comprising:
a vest body of structural material, having an interior surface and an exterior surface, and a periphery;
halo supporting means attached to said vest body;
a lining for said vest body, said lining comprising first and second layers, said first layer adjacent the interior surface of said vest body, and said second layer disposed on the opposite side from said first layer as said vest body;
said first layer comprising a waterproof and vapor proof material that allows lateral movement of air and water vapor with respect thereto; and
said second layer comprising a soft, wicking material of air, water, and vapor permeable material, and means for removably attaching said second layer to said vest body; said second layer being less than about 0.3 inches thick.

2. A halo vest as recited in claim 1 wherein said first layer comprises closed cell foam.

3. A halo vest as recited in claim 2 wherein said foam is cross linked polyethylene foam.

4. A halo vest as recited in claim 2 wherein said foam has means defining grooves therein to facilitate transport of liquid toward the periphery of the vest.

5. A halo vest as recited in claim 2 wherein said second layer comprises a polypropylene bunting material having a thickness of approximately 0.2-0.3 inches.

6. A halo vest as recited in claim 1 wherein means for releasably attaching said second layer to said vest body comprises hook and pile fasteners operatively connected to said vest body interior surface and said second layer.

7. A halo vest as recited in claim 1 wherein said second layer comprises a textile material having a thickness of approximately 0.2-0.3 inches, an MVT of at least about 400 grams/m$^2$ hr., and an air permeability of at least about 175 ft.$^3$/ft.$^2$/min.

8. A halo vest comprising:
a vest body of structural material, having an interior surface and an exterior surface, and a periphery;
halo supporting means attached to said vest body; and
a lining, of wicking material, for said vest body;
said vest body having a surface configuration that avoids pressure on bony prominences, has flat surfaces at flat bone areas and curved surfaces at curved bone areas, of the user, and exerts less than seven pounds per square inch pressure on the wearer's skin, while having no dimension from an interior surface point thereof to the closest peripheral portion thereof larger than the ability of the lining to readily wick liquid from the interior surface point to the peripheral portion, so as to avoid ulcer formations on the wearer's skin.

9. A halo vest as recited in claim 8 wherein the maximum straight line dimension from any interior surface point of the vest body to the closest peripheral portion is less than about four inches.

10. A halo vest as recited in claim 8 wherein the interior surface of the vest body is flat at the wearer's sternum, and curved at the wearer's ribs, covering the sternum and at least part of ribs, and does not engage the wearer's shoulder blades or spinous processes.

11. A halo vest as recited in claim 10 wherein the average distance from each interior point of the vest body to the closest vest peripheral portion is less than about three inches.

12. A halo vest as recited in claim 8 wherein said lining comprises first and second layers, said first layer adjacent the interior surface of said vest body, and said second layer disposed on the opposite side from said first layer as said vest body;
said first layer comprising a waterproof and vapor proof material that allows lateral movement of air and water vapor with respect thereto; and
said second layer comprising a soft, wicking material of air, water, and vapor permeable material, and means for removably attaching said second layer to said vest body; said second layer being less than about 0.3 inches thick.

13. A halo vest as recited in claim 12 wherein said first layer comprises closed cell foam.

14. A halo vest as recited in claim 13 wherein said foam is cross linked polyethylene foam.

15. A halo vest as recited in claim 12 wherein said foam has means defining grooves therein to facilitate transport of liquid toward the periphery of the vest.

16. A halo vest as recited in claim 12 wherein said second layer comprises a textile material having a thickness of approximately 0.2-0.3 inches, an MVT of at least about 400 grams/m$^2$/24 hr., and an air permeability of at least about 175 ft.$^3$/ft.$^2$/min.

17. A halo vest as recited in claim 12 wherein means for releasably attaching said second layer to said vest body comprises hook and pile fasteners operatively connected to said vest body interior surface and said second layer.

18. A halo vest as recited in claim 12 wherein said vest body is made of hard plastic.

19. A method of treating spine and/or neck injuries using a halo vest with a lining having at least two layers including, a first layer closer to the halo vest than the second layer, and the second layer adjacent the patient's skin, comprising the steps of:
(a) in a medical procedure practiced by a health care professional, placing a patient in the halo vest with the halo attached to the patient's head; and
(b) in a non-medical procedure, not practiced by a health care professional, removing only the layer of the vest lining, adjacent the patient's skin, on approximately a daily basis, and replacing the second layer with a clean lining layer while the patient is wearing the halo vest, without removal of the halo vest or jeopardizing the health of the patient.

20. A halo vest for a human wearer, comprising:
a vest body of structural material, having an interior surface and an exterior surface, and a periphery;
halo supporting means attached to said vest body;
a lining for said vest body, said lining comprising at least one layer adjacent the body of the wearer, comprising a soft, wicking material of air, water, and vapor permeable material, and means for removably attaching said layer to said vest body; said layer being about 0.2-0.3 inches thick and having an MVT of at least about 400 grams/m$^2$/24 hr., and an air permeability of at least about 175 ft.$^3$/ft.$^2$/min.

* * * * *